United States Patent [19]

Moberg et al.

[11] Patent Number: 4,800,895
[45] Date of Patent: Jan. 31, 1989

[54] ELECTROENCEPHALOGRAPHIC DATA DISPLAY METHOD AND SYSTEM

[75] Inventors: Richard S. Moberg, Philadelphia, Pa.; Frank W. Sharbrough, Rochester, Minn.

[73] Assignee: Interspec, Inc., Coshohocken, Pa.

[21] Appl. No.: 903,510

[22] Filed: Sep. 3, 1986

[51] Int. Cl.$^4$ .................................................. A61B 5/04
[52] U.S. Cl. ...................................... 128/731; 364/576
[58] Field of Search .................................. 128/731–733, 128/710; 364/576, 551, 554, 570

[56] References Cited

U.S. PATENT DOCUMENTS

| | | | |
|---|---|---|---|
| 4,412,547 | 11/1983 | Callahan et al. | 128/731 |
| 4,424,816 | 1/1984 | Callahan et al. | 128/731 |
| 4,498,080 | 2/1985 | Culver | 128/731 X |
| 4,579,125 | 4/1986 | Strobl et al. | 128/731 |
| 4,592,369 | 6/1986 | Davis et al. | 128/733 |

*Primary Examiner*—Kyle L. Howell
*Assistant Examiner*—Angela D. Sykes
*Attorney, Agent, or Firm*—Ratner & Prestia

[57] ABSTRACT

A novel display method and system for electroencephalographic data includes the use of a linear array of picture elements whose distance from each other is inversely proportional to the power of the EEG signal at a given frequency. The display indicates relative proportions of power over a range of frequencies of interest.

21 Claims, 7 Drawing Sheets

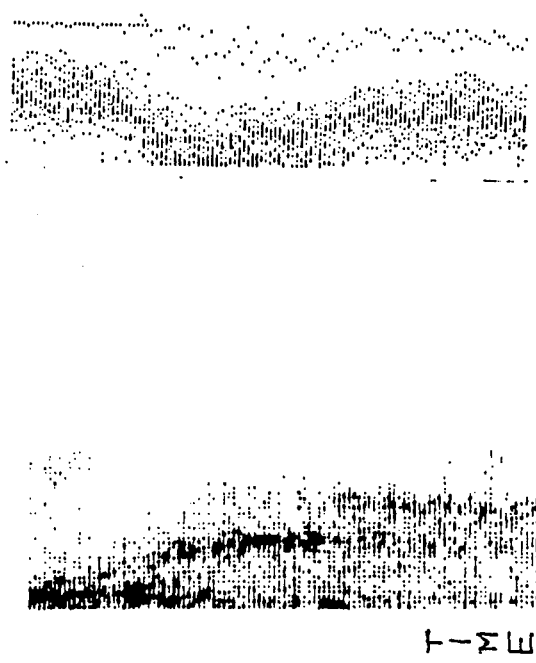
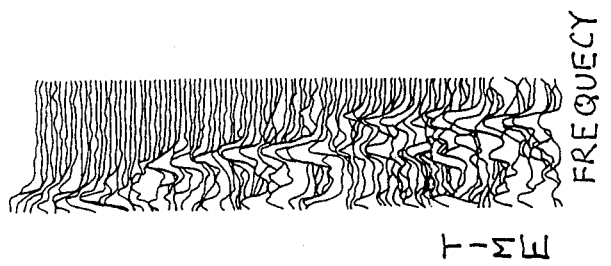
FIG.2E
FIG.2B
PRIOR ART
FIG.2A
PRIOR ART

ELECTROENCEPHALOGRAPHIC DATA DISPLAY METHOD AND SYSTEM

The present invention relates to the field of electroencephalography, and signal processing and displays therefor.

BACKGROUND OF THE INVENTION

The use of electroencephalogram information as an intraoperative monitor is well established in the medical literature. As noted by Levy, et al. *Anesthesiology,* Volume 3, September, 1980, pages 223–226), electroencephalogram (EEG) data is useful in monitoring during cerebrovascular surgery. Other relationships between the EEG data and cerebral ischemia, as well as central nervous system changes, have been noted.

Recent innovations in signal processing and display techniques for EEG data have increased the usefulness of this diagnostic tool in the operating room. Automated gain adjustment, automated electrode impedance checking and artifact detection relieve substantial amounts of the routine workload associated with operation of electroencephalographic monitoring equipment. Furthermore, concise displays conveying several minutes of EEG data aid in the interpretation of this data by physicians in the operating room.

Of these areas of advance in EEG technology, the display has been given much attention. Because of the relatively high volume of information which must be conveyed to the physician, and the period of time over which subtle changes in the presented information may occur, various presentation and display schemes have been developed in the prior art. In order to understand the various display schemes employed, a basic understanding of the nature of the EEG signal is necessary.

The electroencephalographic signal has typically been recorded as a voltage on a strip chart recorder. The wave form thus recorded displays several important frequency components. In addition, various artifacts are displayed which change the minute voltages being recorded. EEG activity commonly is in the range of 10 to 25 microvolts and is thus sensitive to changes in external conditions. In addition, voluntary and involuntary muscle response, and central nervous system changes, significantly affect EEG readings.

A problem with the strip chart method of recording EEG data arises because subtle changes in the baseline may be separated by 20 or more pages of paper tracings and thus be difficult or impossible for the physician to detect.

In an effort to achieve more useful data displays, the prior art has developed various data transformations. The Compressed Spectral Array (CSA) (shown in FIG. 2A) employs a plot of power versus frequency for discrete time intervals or epochs of analysis. The plotted power/frequency curves are then processed in a hidden line removal algorithm in order to provide a "hill-and-valley" display. Hills representing high power at a given frequency may be interpreted as they change in contour and location on the surface described by a series of plots. Typically, series of power/frequency lines is displayed on a cathode ray tube or printed on a paper chart. Typical of commercial analyzers using the CSA technique are the Model 1263 Berg Fourier Analyzer marketed by OTE Biomedica, Pathfinder by Nicolet, EEG Trend Monitor by Nihon Kohden, and Neurotrac ™ from Interspec, Inc., the assignee of the present application.

The CSA technique suffers from inherent loss of displayed data due to the hidden line processing employed in the display unit. Epochs of high energy necessarily obscure earlier epochs (or later epochs depending on the display format) having lower energy content and thus reduce the amount of usable data available to the attending physician.

A similar display technique which does not suffer from the hidden line problem is the Density Spectral Array (DSA) display. (Shown in FIG. 2B) In this display technique, each epoch has power displayed as a dot of a given optical density. Higher power at a given frequency is signified by the placement of a darker, more dense dot while lower power is signified by a small and lighter density dot. Because no Y-axis excursions are plotted, no hidden line removal need be performed and, therefore, no data is obscured. However, inherent variability in the output device, along with the difficulties inherent in perception and quantification of shades of gray, make DSA displays imprecise and complicated to use. A commercially available electroencephalographic monitoring device which employs the DSA technique is the Cerebrotrac 2500 from SRD Advanced Instrumentation. Instead of using the density of dots to indicate levels of power, another technique is to use different colors. The color density plots are employed on the Nomad by Tracor, Inc. and also on the Cerebrotrac by SRD. Problems with color displays such as this are the same as with DSA, with the addition of their inability to be correctly interpreted by color-blind individuals (a high percent of males).

Yet another data display technique in commercial use today is that exemplified by the Cerebral Tracer from CNS Inc. (Shown in FIG. 2D) In this device, colors correspond to the four clinical frequency ranges of the EEG signal (i.e., red=delta; yellow=theta; green=alpha; blue=beta). Sixteen channels of data are simultaneously displayed as a series of pie charts superimposed over a schematic representation of the hemispheres of the patient's brain. Relative contribution of each frequency band to total signal is indicated by the included angle of the colored sector displayed for that frequency. Total power is indicated as a function of the pie chart's total area. While the instantaneous display attainable with such a technique may be useful, it lacks a trend over time feature. The manufacturer of the Cerebral Tracer instrument, therefore, also include a trend display which presents color-coded histograms for each EEG channel. While such time-displayed histograms may convey trend data, they fail to convey the full amount of data which is desirably presented to the attending physician.

Finally, the Life Scan EEG monitor from Neurometrics displays five frequency ranges in color using a modified DSA display technique. In this device, the successive epochs are displayed on a "tilted plane." (Shown in FIG. 2C) The plane gives the viewer the impression of viewing the data from above and to the right of the origin of the plot. The result of such a plot is that less information is obscured by more recent and more energetic epochs. However, the difficulties of interpretation inherent in DSA and CSA are still evident in the Life Scan device.

Despite the numerous advances in electroencephalographic signal interpretation and display, there still exists a significant need for a readily understandable display for long-term EEG data.

BRIEF DESCRIPTION OF THE INVENTION

Because of the importance of being able to detect subtle changes in specific parameters of the EEG in patients undergoing surgical procedures where blood supply to the brain might be compromised, data processsing and analysis by automated techniques are essential for the use of EEG monitors in the operating room.

The system and method of the present invention presents the attending physician with a display comprised of multiple lines of unevenly spaced dots. The distance from a dot to the next adjacent dot within a line is inversely proportional to the amount of power represented by that dot at that frequency.

The present invention derives the display by determining the total power of an EEG signal during a predetermined time period, dividing the total power by a resolution to yield a step value, and then calculating a running sum of power at each frequency. Whenever the running sum exceeds an integer multiple of the step value, a dot is placed on the display at the corresponding frequency location on the axis.

The present invention improves on the prior art display processes by providing a greater degree of data compression in a concise, easy to interpret format, while not obscuring any data or trend information. The Spectral Power Percentile Array (SPPA) display technique of the present invention permits such high levels of data compression while retaining all data as visibly indicated signals, both on a display screen and, optionally, on a printed paper output.

BRIEF DESCRIPTION OF THE FIGURES

FIG. 2A is a diagram of a typical display of an electroencephalograph using CSA techniques.

FIG. 2B is a diagram of a typical display of an electroencephalograph using DSA techniques.

FIG. 2E is a diagram of a typical display of an electroencephalograph using the SPPA techniques of the present invention.

DETAILED DESCRIPTION OF THE INVENTION

Figure 1:
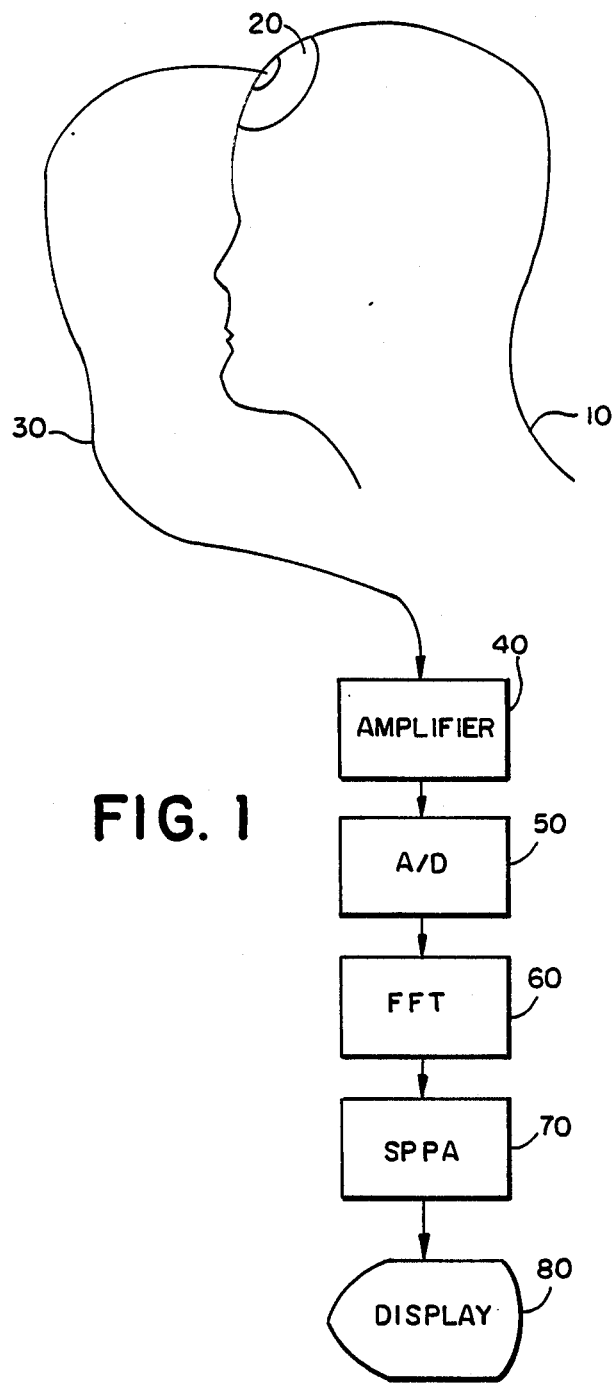
FIG. 1 is a block diagram of the electroencephalographic monitoring and display system of the present invention.

Referring now to FIG. 1, there is shown an overall block diagram of the system of the present invention. For the derivation of electroencephalographic signals, patient 10 is fitted with one or more electrodes 20 which are affixed to the scalp. Each electrode is usually affixed in a predetermined area and, together with a ground or reference electrode, constitutes the transduction means for one channel of electroencephalographic data. In the following discussion, only one channel and electrode will be referred to. It will be understood by those skilled in the art, however, that multiple electrodes are commonly affixed to the patient and multiple channels of electroencephalographic data are commonly recorded and processed.

Electrode 20 is connected via electrical cable 30 to a signal amplifier 40. Amplifier 40 amplifies the minute electrical potentials derived from electrode 20 (commonly several microvolts) for further signal processing. The amplified signal is then processed by analog-to-digital converter 50 in order to arrive at a digital representation of the electroencephalographic voltage waveform.

Figure 2C:
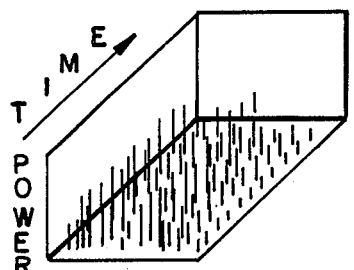
FIG. 2C is a diagram of a typical display of an electroencephalograph using tilted plane DSA techniques.
Figure 2D:
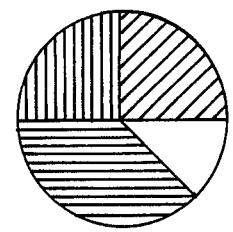
FIG. 2D is a diagram of a typical display of an electroencephalograph using techniques exemplified by the Cerebral Tracer from CNS Inc.

The digitized waveform is processed by Fast Fourier Transform means 60 and the results of the transform are subsequently processed by Spectral Power Percentile Array means 70 and output for display on display 80. Display 80 commonly comprises multiple display means including video displays and various types of recorders and printers of the type commonly employed for graphical output. FIG. 2E depicts a typical displayed result of the present invention.

Figure 4:
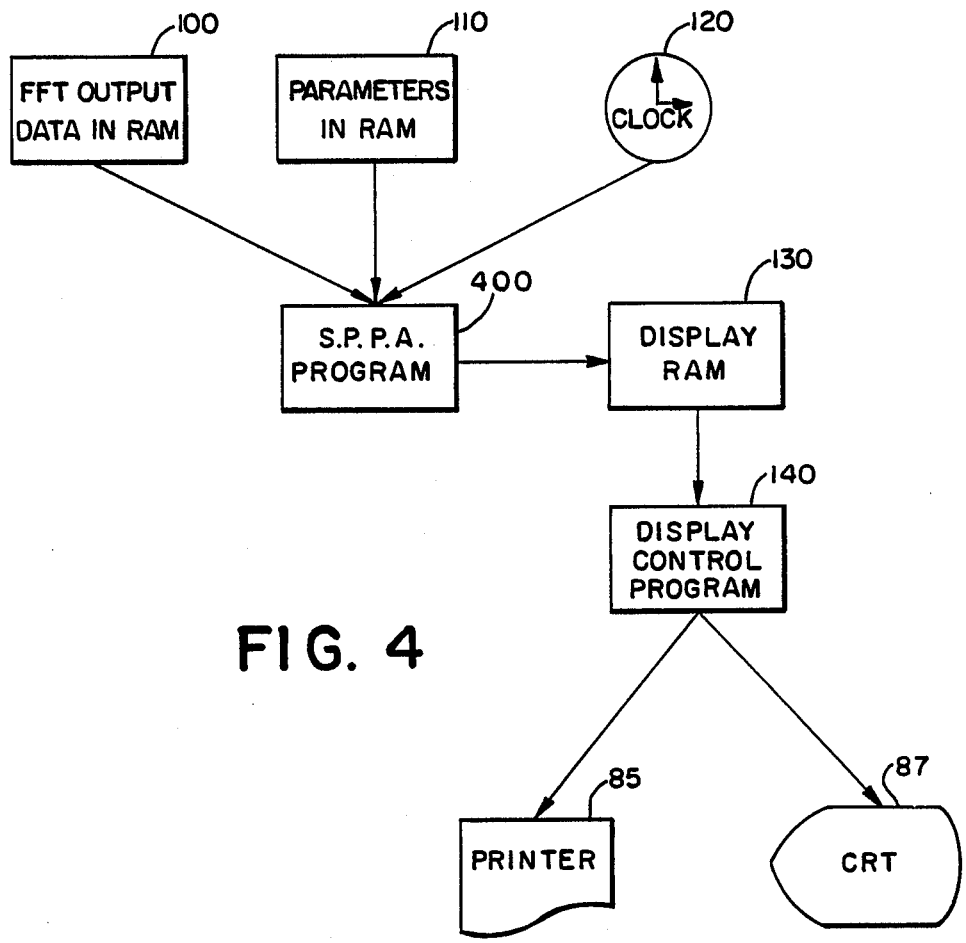
FIG. 4 is a block diagram of the internal architecture of the electroencephalogram monitor system of the present invention.
Figure 3:
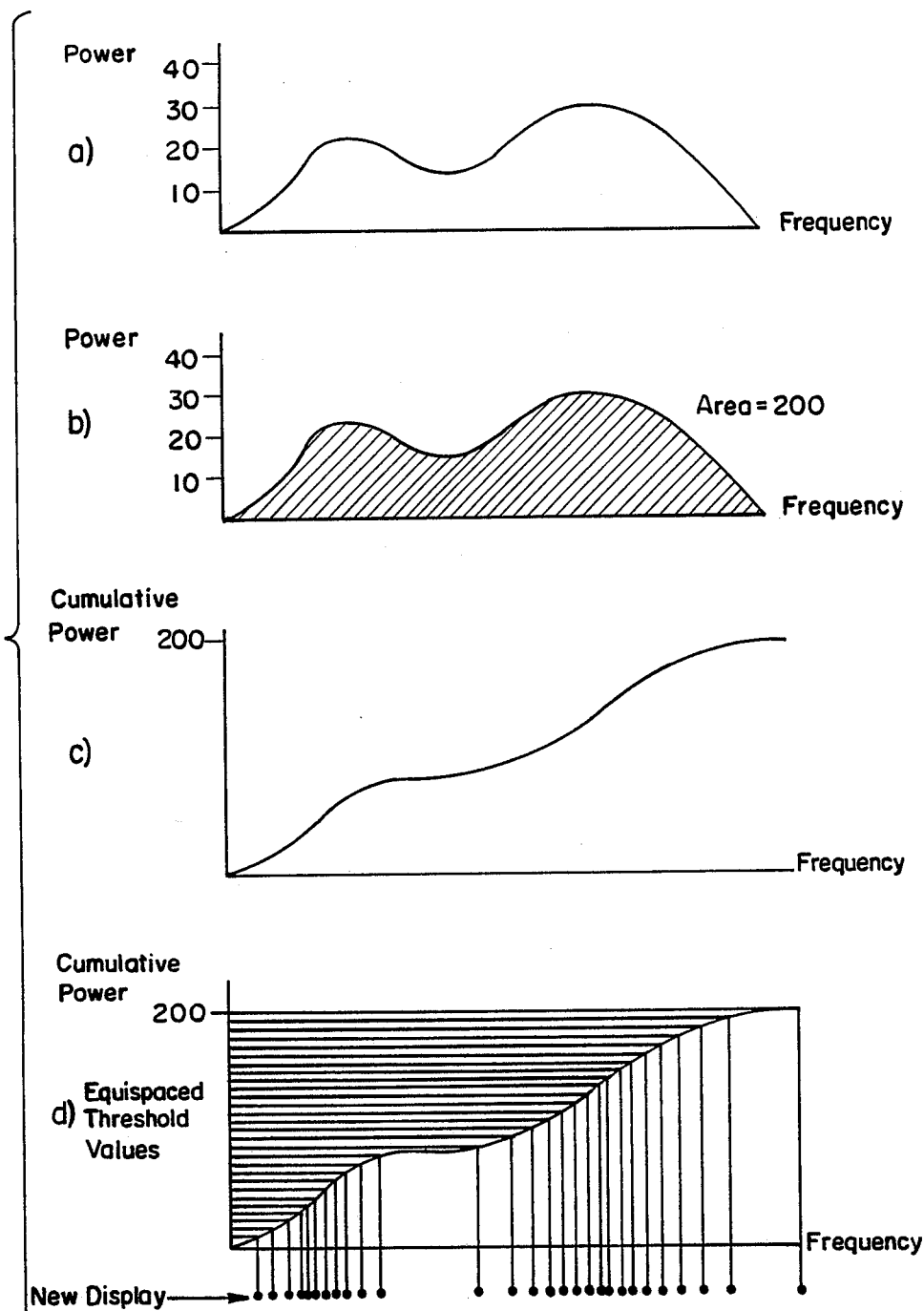
FIG. 3 is a series of graphs representing the EEG signal at various stages during its processing according to the present invention.

Referring now to FIG. 4, there is shown a more detailed block diagram of the signal processing system 70 of the present invention. Signals which have been processed through amplifier 40, A-to-D converter 50, and Fast Fourier Transform means 60 are represented by block 100 as output data stored in random access memory, which is accessible to the Spectral Power Percentile Array program means 400. FIG. 3a depicts a smoothed plot of this stored data as a power versus frequency curve during one time period or epoch. Also accessible to SPPA program means 400 are various system parameters indicative of system configuration, operating environment, and other variable data These parameters 110 are also stored in random access memory. Finally, a clock means 120, which may be either a common counter circuit or a real-time clock, is accessible to SPPA program means 400. Using data 100, parameters 110, and signals from clock 120, SPPA program means 400 places a transformed representation of the original electroencephalographic signal into display random access memory 130.

Signal processing system 70 creates a display such as that shown in FIG. 2E by transforming an electroencephalographic signal according to the following steps: The transduced, amplified, digitized, and Fourier transformed signal plotted in FIG. 3a, is summed to yield a total power indication. Each time period or epoch is processed sequentially. The total power for an epoch is depicted as the shaded area under the curve of FIG. 3b.

After total power has been determined, a running sum of total power is calculated for each frequency present in the signal. This running sum is depicted as the function plotted in FIG. 3c.

In order to derive the Spectral Power Percentile Array display of the present invention, the running sum of total power for a given epoch is subdivided into small ranges (of, for example, 5% of the total power each.) For each successive range, the running sum of total power is compared to that range's percentage of the total power calculated above. Every time the running sum exceeds the calculated percentage of total power, a small dot is displayed at a position which corresponds to that frequency in the original EEG signal. This series of comparisons is depicted in FIG. 3d as a series of horizontal lines drawn from the Y-axis to the plotted cumulative power function, and the projected vertical lines drawn from the intersection of the function and the horizontal lines to the X-axis, and then extended to a series of plotted dots below the X-axis. (A series of these lines of dots, plotted over time, is the display shown in FIG. 2E.

Display control program means 140, which also has access to display random access memory 130, then directs a visual representation of the transformed electroencephalographic signal to either output printer 85 or output cathode ray tube 87.

Figure 5:
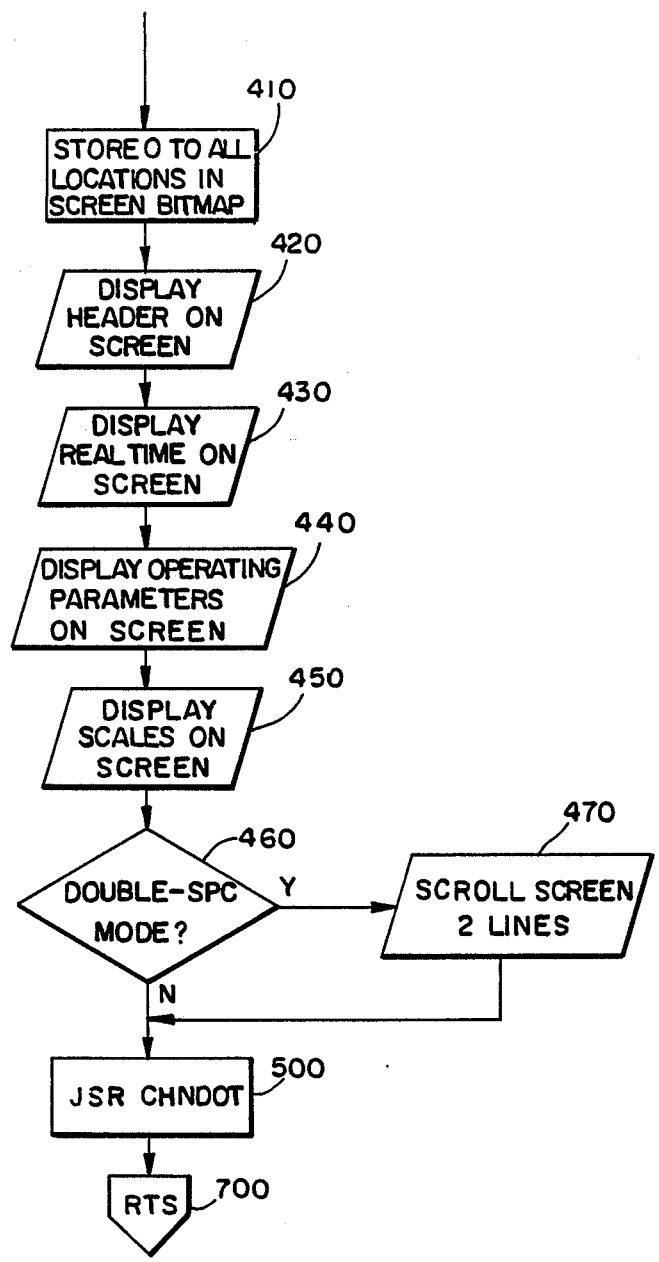
FIGS. 5–7 are detailed flow diagrams of the method of the present invention.

Referring now to FIG. 5, there is shown a detailed flow diagram of display control program 140. Upon entry, display control program 140 first stores a zero constant to all memory locations in display random access memory 130 which constitute a bit map of the cathode ray tube screen After zeroing the bit map at block 410, the display control program then fetches and stores that portion of the bit map which constitutes the screen heading information at block 420, displays a time of day indication at block 430, displays the current operating parameters according to which the SPPA program means 400 is processing data at block 440, displays appropriate axes or scales on screen at block 450, and determines at block 460 whether a double-spacing mode which permits less data compression to be achieved is in effect. If the double-spacing mode is found to be in effect, a scroll or increment of a line counter for two lines is carried out at block 470. Finally, a jump to a subroutine known as CHNDOT for fetching and displaying of a line of processed electroencephalographic data occurs at block 500. The control program returns to a calling program (not shown) upon completion of the CHNDOT routine.

Figure 6:
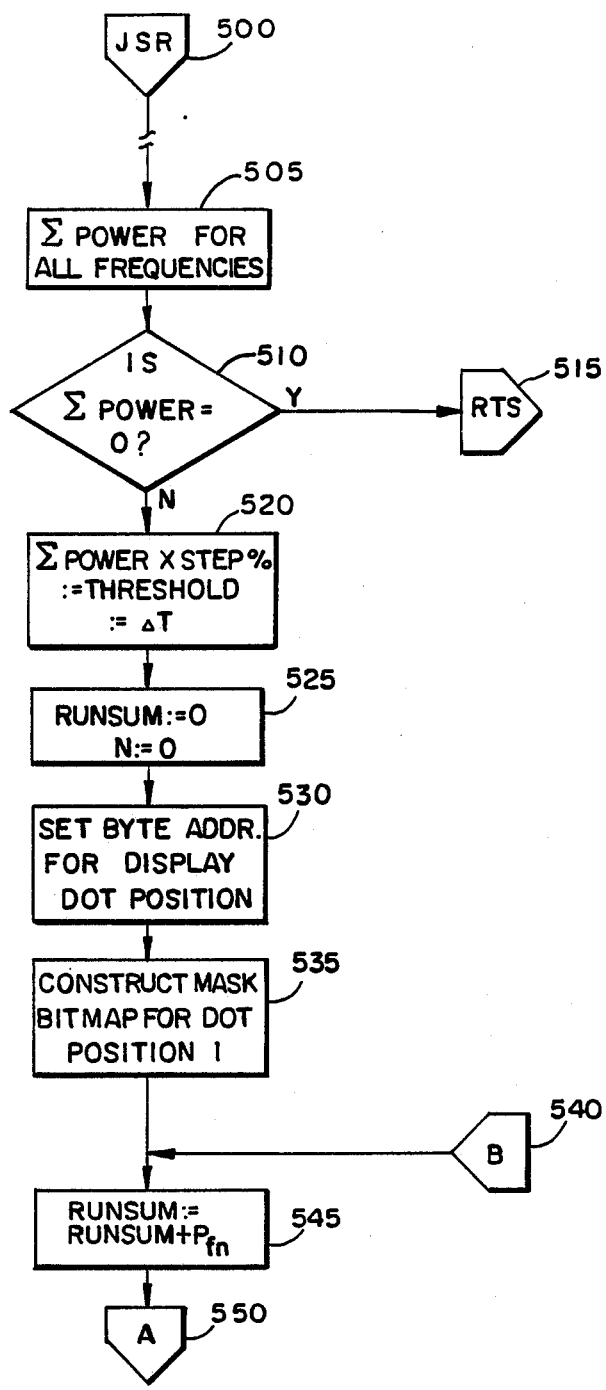

Referring now to FIG. 6, there is shown a detailed flow diagram for the routine CHNDOT which is the central routine of SPPA program means 400. The entry to CHNDOT occurs at the jump to subroutine connector 500 which is identical to block 500 of FIG. 5.

After various conventional initializations (not shown), the total power for all frequencies represented during a particular epoch of electroencephalographic signal is calculated at block 505. FIG. 3*b* depicts this operation as an integration of the waveform of FIG. 3*a*. At block 510, a decision is made which assures that some signal is present. If the total power for a channel of EEG data is zero, the YES branch results in a return at block 515 to the calling routine. If total power is not zero, the total power is subdivided by a predetermined step percentage and assigned to both a threshold variable and a *delta* T at block 520. The running sum of accumulated power and the variable N are then initialized to zero value at block 525.

At block 530, a byte address in display random access memory is set as a base address for display of the next dot indicative of accumulated power. At block 535, a mask bit map is constructed for selection of the appropriate display bit within the byte addressed at block 530. Block 545 is the beginning of the power accumulation loop for determination of the next displayed dot along the X axis of the display. The running sum of accumulated power is incremented by the addition of the power for the next incremental frequency. FIG. 3*c* depicts the running sum function for the waveform of FIG. 3*a*. This power, it will be recalled, is stored as a digital result of the Fast Fourier Transform of the electroencephalographic signal. Processing continues at offpage connector 550, labeled A.

Figure 7:
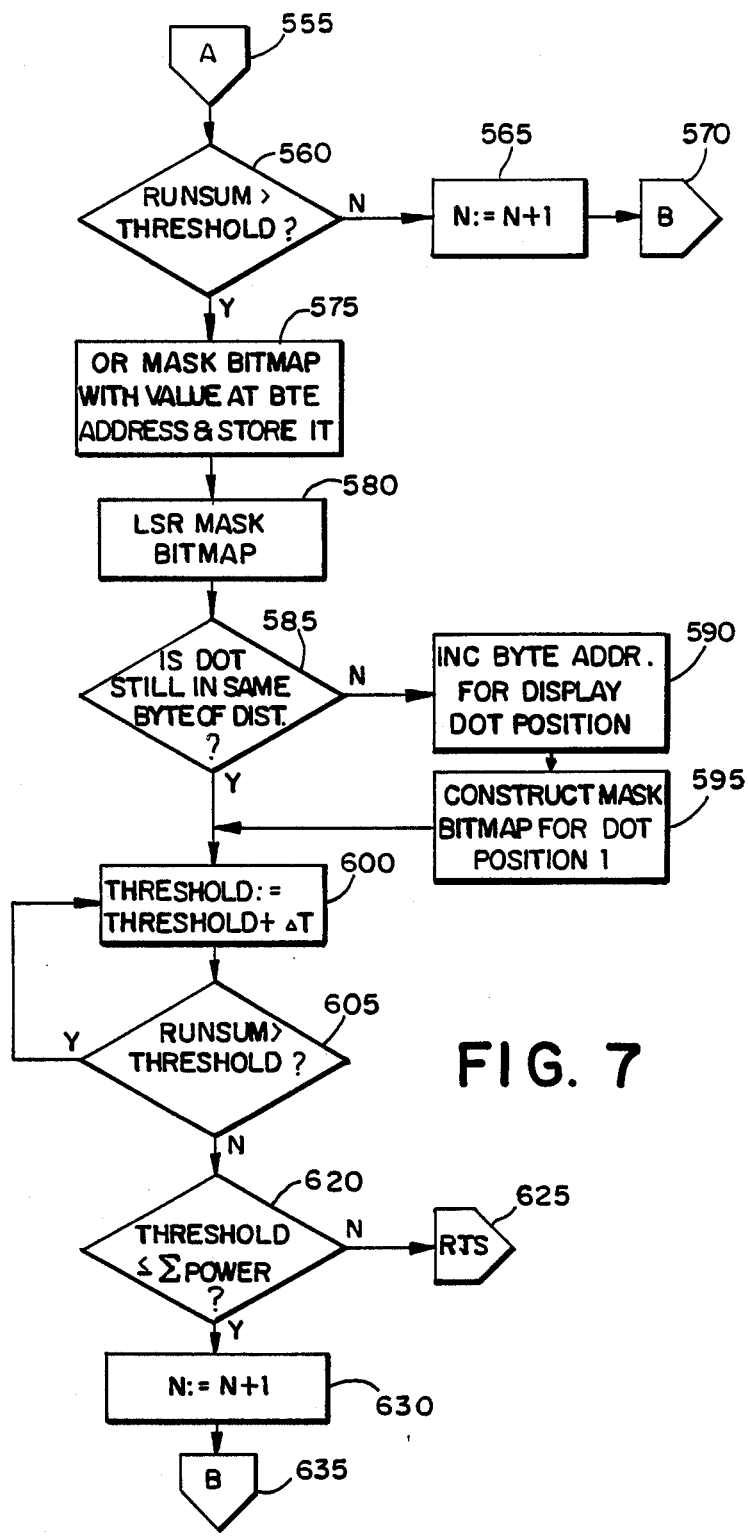

Referring now to FIG. 7, processing continues on onpage connector 555, labeled A. At block 560, a determination is made of whether the newly incremented running sum of power is greater than the threshold value determined earlier. If it is not, the N counter is incremented at block 565 and processing resumes at offpage connector 570, labeled B. Onpage connector 540, also labeled B, brings about an iteration of the procedure just described for blocks 545 through 560. In the event that determination 560 is affirmative, the mask bit map is OR'ed with the value at the byte address for dot display and is stored in that byte. This has the effect of setting a one-bit which will be interpreted by display control program 140 as a bright pixel on the display screen or a darkened pixel on the output display printer. After storing the bit indicative of dot position, the mask bit map is logically shifted right to provide the next bit position for display at block 580. FIG. 3*d* is a complete representation of the dot positions which result from iteration of this accumulation process.

Block 585 is a determination of whether a byte boundary is crossed by a ninth shift of the mask bit map. If such a byte boundary has been crossed, the byte address for the newly determined display position is incremented at block 590 and the bit map for dot position 1 is reconstructed at block 595. At block 600, the threshold used for determination of next displayed dot position is incremented by the *delta* T amount determined earlier. Finally, at block 605, a determination of whether the sum has crossed more than one threshold is made. If so, the threshold is again incremented at block 600 until the running sum is less than the desired threshold amount.

At block 620, a determination of whether the threshold remains less than or equal to the total power measured for the epoch is made. If the threshold is not less than the total power or equal to it, the routine terminates because all thresholds have been crossed. Termination is via a Return From Subroutine 625 to the calling routine. If the threshold power is still less than or equal to the total power computed, the variable N is incremented at block 630 and processing continues at offpage connector 635, labeled B. The loop then continues at onpage connector 540, labeled B, for yet another iteration.

By operating through these series of steps just described, a novel display is derived. The placement of dots along the X axis is determined by the cumulative summation of the power within the signal. Thus, the density of dots along the X axis is proportional to the power represented by a given frequency within the electroencephalographic signal. As an example, if a step % of 5 is chosen, an epoch will be divided into 19 sections. The distance from any given dot to the next adjacent dot along the X axis is directly proportional to the inverse of the power represented by that frequency within the EEG signal. Thus, a more rapid occurrence of dots along the axis is indicative of higher power contribution by those frequency bands, while a sparse dot distribution is indicative of low power.

The derivation of the dot-density to the original waveform of the electroencephalographic data may be derived by examining the frequencies corresponding to displayed dots.

For a sequence of frequencies represented as dots $D_0$, $D_1, D_2 \ldots D_n$ where A is the number of intervals represented, A' is the area of an interval or $$(A \cdot 1/n+1).$$

The value of the midpoint of the segment of the original function S(f) bounded by frequencies $D_n$ and $D_{n-1}$ is:

$$S \frac{D_n - D_{n-1}}{Z} = \frac{A'}{D_n - D_{n-1}}$$

This Spectral Power Percentile Array method of the present invention does not suffer from the inherent lack of precision of gray scale output devices, does not obscure data in less energetic earlier epochs, and is visually similar to those display techniques already in use by physicians.

The foregoing has set forth an exemplary and preferred embodiment of the present invention. It will be understood, however, that various alternatives will occur to those of ordinary skill in the art without departure from the spirit and scope of the present invention.

It is claimed:

1. A method for displaying electroencephalographically derived signals comprising transducing of said signals from a patient, transmitting of said signals to an amplifier for amplification, digitizing of said amplified signals by an analog-to-digital converter, quantizing of said digitized signals into discrete frequency components by Fourier transformation, display processing of said quantized signal, and displaying of visual representations of said processed signal on a visual output device, wherein said display processing includes the steps of:
   (a) determining the total power of said quantized signal during a predetermined time period or epoch;
   (b) dividing said determined total power by a predetermined number representative of desired display resolution to yield a step value;
   (c) establishing a running total power indication for accumulating said quantized signal values;
   (d) until said running total power indication exceeds said computed total power: (1) repeatedly adding quanta of said signal to said running total power indication, and (2) comparing said running total power indication to an an integer multiple of said step value, and
      (i) if said running total power indication exceeds said multiple of said step value, displaying a visual indication at a position corresponding to said integer multiplier on said visual output device, incrementing said integer multiplier, and repeating step (d); or
      (ii) if said running total power indication does not exceed said integer multiple of said step value, repeating step (d).

2. The method of claim 1 wherein said epoch is determined by reference to an internal timer.

3. The method of claim 5 wherein said epoch is from 0.5 seconds to 20 seconds in duration.

4. The method of claim 1 further including displaying of a line or lines of textual header information on said visual output device.

5. The method of claim 1 further including displaying of an indication of time and/or date on said visual output device.

6. The method of claim 1 further including displaying of operational parameters comprising, one or more of: said step value, said epoch duration, indication of current output devices, and information identifying said patient, on said visual output device.

7. The method of claim 1 further including displaying a representation of said determined total power on said visual output device.

8. The method of claim 1 wherein displaying of visual representations of said processed signal on a visual output device comprises storing a value indicative of a displayed picture element in a memory mapped display buffer.

9. The method of claim 8 wherein displaying of visual representations of said processed signal on a visual output device further includes computing a location for storing said value in said buffer, said location corresponding to a predetermined position on said visual output device.

10. A system for displaying electroencephalographically derived signals comprising signal transduction means for deriving electroencephalographic signals from a patient, transmitting means for communicating said signals to an amplifier means for amplification, analog-to-digital converter means for digitizing of said amplified signals, Fourier transformation means for quantizing of said digitized signals into discrete frequency components, display processing means and display means, said display processing means including means for:
   (a) determining the total power of said quantized signal during a predetermined time period or epoch;
   (b) dividing said determined total power by a predetermined number representative of desired display resolution to yield a step value;
   (c) establishing a running total power indication for accumulating said quantized signal values;
   (d) repeatedly until said running total power indication exceeds said computed total power: (1) adding quanta of said signal to said running total power indication, and (2) comparing said running total power indication to an an integer multiple of said step value, and determining whether said running total power indication exceeds said multiple of said step value, and,
      (i) if the results of said determination are affirmative, then displaying a visual indication at a position corresponding to said integer multiplier on said visual output device, incrementing said integer multiplier, and branching to repeat; or
      (ii) if the results of said determination are negative, then branching to repeat.

11. The system of claim 10 wherein said display means is an all-points-addressable device having a corresponding memory-mapped display buffer.

12. The system of claim 11 wherein said buffer is bit-mapped.

13. The system of claim 12 wherein said integer multiplier is a pointer to a predetermined bit in said display buffer bit-map.

14. The system of claim 10 further including means for displaying of a line or lines of textual header information on said display means.

15. The system of claim 10 further including means for displaying of an indication of time and/or date on said display means.

16. The system of claim 10 further including means for displaying of operational parameters comprising, one or more of: said step value, said epoch duration, indication of current output devices, and information identifying said patient, on said display means.

17. The system of claim 10 further including means for displaying a representation of said determined total power on said display means.

18. The system of claim 10 wherein said total power determining means comprises a timer for defining said time period or epoch.

19. The system of claim 18 wherein said timer is a real-time clock.

20. The system of claim 18 wherein said epoch is from 0.5 seconds to 20 seconds in duration.

21. An electroencephalograph system comprising:

sensing means for developing signals indicative of nervous system function over a predetermined period of time;

means responsive to said signals for developing signals indicative of the power of said signals at predetermined frequencies;

means for summing said signals representative of power to derive the total power of said signals;

means for dividing said total power into a predetermined number of intervals;

means for comparing the power represented by the running sum of said power signals for a given interval with a threshold value;

means responsive to said comparison means for developing a visual indication where said running sum exceeds said threshold value for said given interval; and visual display means for communicating said developed indication to a user.

* * * * *

UNITED STATES PATENT AND TRADEMARK OFFICE
CERTIFICATE OF CORRECTION

PATENT NO. : 4,800,895
DATED : January 31, 1989
INVENTOR(S) : Richard S. Moberg et al It is certified that error appears in the above—identified patent and that said Letters Patent is hereby corrected as shown below:

Column 7, line 64 (Claim 3, line 1) cancel "5" and insert --2--.

Signed and Sealed this

Fourth Day of July, 1989

Attest:

DONALD J. QUIGG

Attesting Officer

Commissioner of Patents and Trademarks